(12) United States Patent
Mallary

(10) Patent No.: US 7,182,844 B1
(45) Date of Patent: Feb. 27, 2007

(54) LACTOSE TEST APPARATUS

(76) Inventor: Michael Mallary, 4 Matthew La., Sterling, MA (US) 01564

( * ) Notice: Subject to any disclaimer, the term of this patent is extended or adjusted under 35 U.S.C. 154(b) by 625 days.

(21) Appl. No.: 10/444,657

(22) Filed: May 23, 2003

Related U.S. Application Data

(60) Provisional application No. 60/383,307, filed on May 28, 2002.

(51) Int. Cl.
*G01N 27/327* (2006.01)
*G01N 21/00* (2006.01)
*B32B 5/02* (2006.01)

(52) U.S. Cl. .................. 204/403.01; 204/403.14; 422/56; 422/82.05

(58) Field of Classification Search ............ 204/403.01–403.15; 205/777.5, 778; 422/56, 422/57, 82.05, 82.06; 435/14, 25, 4
See application file for complete search history.

(56) References Cited

U.S. PATENT DOCUMENTS

| | | |
|---|---|---|
| 4,545,382 A | 10/1985 | Higgins et al. |
| 4,711,245 A | 12/1987 | Higgins et al. |
| 5,296,192 A | 3/1994 | Carroll et al. |
| 5,509,410 A | 4/1996 | Hill et al. |
| 5,682,884 A | 11/1997 | Hill et al. |
| 5,727,548 A | 3/1998 | Hill et al. |
| 5,820,551 A | 10/1998 | Hill et al. |

OTHER PUBLICATIONS

Fumio et al. ("Simultaneous determination of glucose and lactose in sour milk using an immobilized glucose oxidase electrode combined with a .beta.-galactosidase-attached measuring cell," Bunseki Kagaku (1990), 39(11), 729-34).*
Entry for Beta-Galactosidase of *Escherichi coli* in Encylcopedia of Molecular Biology, John Wiley & Sons, Inc. 1999.*
Sánchez-Mazanares et al. ("Determination of lactose by an enzymatic method," Food Chemistry 46(1993) 425-427).*
Loechel et al. ("Amperometric bi-enzyme based biosensor for the determination of lactose with an extended linear range," Z. Lebensm Unters Forsch A (1998) 207:381-385).*
Katsu et al. (Simultaneous Determination of Lactose and Glucose in Milk using two working enzyme electrodes, Talanta, vol. 41, No. 6 pp. 843-848).*
Photos of two spectrophotometer cells from Analytical Instruments, LLC. downloaded on May 15, 2006.*
Entry for "Galactosidase, β-" in the ACS Registry, downloaded May 15, 2006.*
Ernest C. Adams, Jr., C. Edwzard Burkhart, and Alfred H. Free, Specificity of a Glucose Oxidase Test for Urine Glucose, Science magazine, pp. 1082-1083, 1957.
Wendell T. Caraway, PH.D. and Nelson B. Watts, M.S., Carbohydrates, pp. 422-447.

* cited by examiner

*Primary Examiner*—Alex Noguerola

(57) ABSTRACT

A test for the presence of lactose in a sample, in which the test comprises a) treating the sample with lactase enzyme thus converting the lactose into glucose and galactose b) testing the sample for the presence of glucose using any one of a variety of prior art tests for the presence of glucose.

21 Claims, 5 Drawing Sheets

LACTOSE TEST APPARATUS

CROSS-REFERENCE TO RELATED APPLICATIONS

This application claims the benefit under 35 U.S.C. §119 (e) of prior U.S. Provisional Application No. 60/383,307 filed May 28, 2002, which is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

The present invention relates to testing of the presence of lactose in foods.

BACKGROUND

Though approximately 25% of Americans become lactose intolerant as they age, the food industry does not clearly label the presence of lactose in the vast majority of processed foods that contain it. In many cases even euphemisms for lactose such as "Natural Ingredients" are absent from the list of ingredients on the label. Therefore the lactose intolerant consumers cannot avoid becoming ill with any degree of certainty on a day to day basis. The situation is even more intractable in restaurants where there is seldom any detailed information on the lactose content of the menu items. Therefore lactose intolerant individuals have need for a convenient lactose test with which they can screen the foods that they eat.

It is the purpose of the present invention to provide a simple and convenient test for the presence of lactose in every day food items. Many similar tests exist in the market place for the presence of glucose in the blood or urine of diabetics. For example Clinistix reagent strips for urinalysis are manufacture by Bayer Corporation and the principles of operation are taught by Adams et al. [1]. These test strips rely upon a visual assessment of color change by the user in order to assess the concentration of glucose in the sample being tested. More quantitative results for blood concentration of glucose are obtained with the test strips and a read out apparatus produced by MediSence Corporation [2], [3]. This test relies on the enzyme glucose oxidase to convert glucose into gluconic acid and hydrogen peroxide. The test apparatus then detects the hydrogen peroxide by measuring the electrolytic conductance of the sample after a stabilization period of approximately 30 seconds. A blood glucose test is also manufactured by CVS Pharmacy Corporation [4 10]. It relies upon a change in infrared absorption of the sample after treatment with suitable reagents.

Despite the relative rarity of diabetes relative to lactose intolerance there is no available test kit in the market place. The present invention provides for this need by using prior art glucose tests in combination with unique sample treatment to effect a suitable test for lactose.

REFERENCES

[1] Adams, E. C., Burkhart, E., and Free, A. H.: Specificity of a glucose oxidase test for urine glucose. Science 125, 1082–1083, 1957.

[2] U.S. Pat. No. 4,545,382.
[3] U.S. Pat. No. 4,711,245.
[4] Caraway, W. I., "Carbohydrates" in Fundamentals of Clinical Chemistry, Tietz N W, ED., Philadelphia Pa., Sanders, 1976.
[5] U.S. Pat. No. 5,296,192
[6] U.S. Pat. No. 5,509,410
[7] U.S. Pat. No. 5,682,884
[8] U.S. Pat. No. 5,820,551
[9] U.S. Pat. No. 5,727,548

SUMMARY OF THE INVENTION

One aspect of the invention relates to a test for lactose which comprises a) treating the sample with lactase enzyme thus converting the lactose into glucose and galactose b) testing the sample for the presence of glucose using any one of a variety of prior art tests for the presence of glucose. In a preferred embodiment of the invention the test procedure can detect the presence of lactose despite the presence of glucose in the sample. This preferred embodiment comprises a) subjecting a first subsample of the food to a quantitative test for glucose and b) treating a second subsample with lactase enzyme and c) subjecting the second subsample to the same quantitative glucose test as the first said subsample and d) quantitatively comparing the results of the two test to detect an increase in the glucose content of the second said subsample above that of the first said subsample.

Another embodiment of the invention comprises a) subjecting a sample to a quantitative test for glucose and b) adding lactase enzyme to the sample while it is still in the glucose test apparatus and c) detecting an increase over time of the glucose reading due to the conversion of lactose in to glucose.

DETAILED DESCRIPTION OF THE FIRST PREFERRED EMBODIMENTS OF THE INVENTION

We first briefly describe the drawings for the first preferred embodiment.

FIG. 1 shows a schematic drawing of a preferred embodiment of the present invention that is based on an electrolytic technique for detecting glucose.

FIG. 2 shows test cells 10 and 20 formed on a disposable plastic strip 8.

Figure 1:
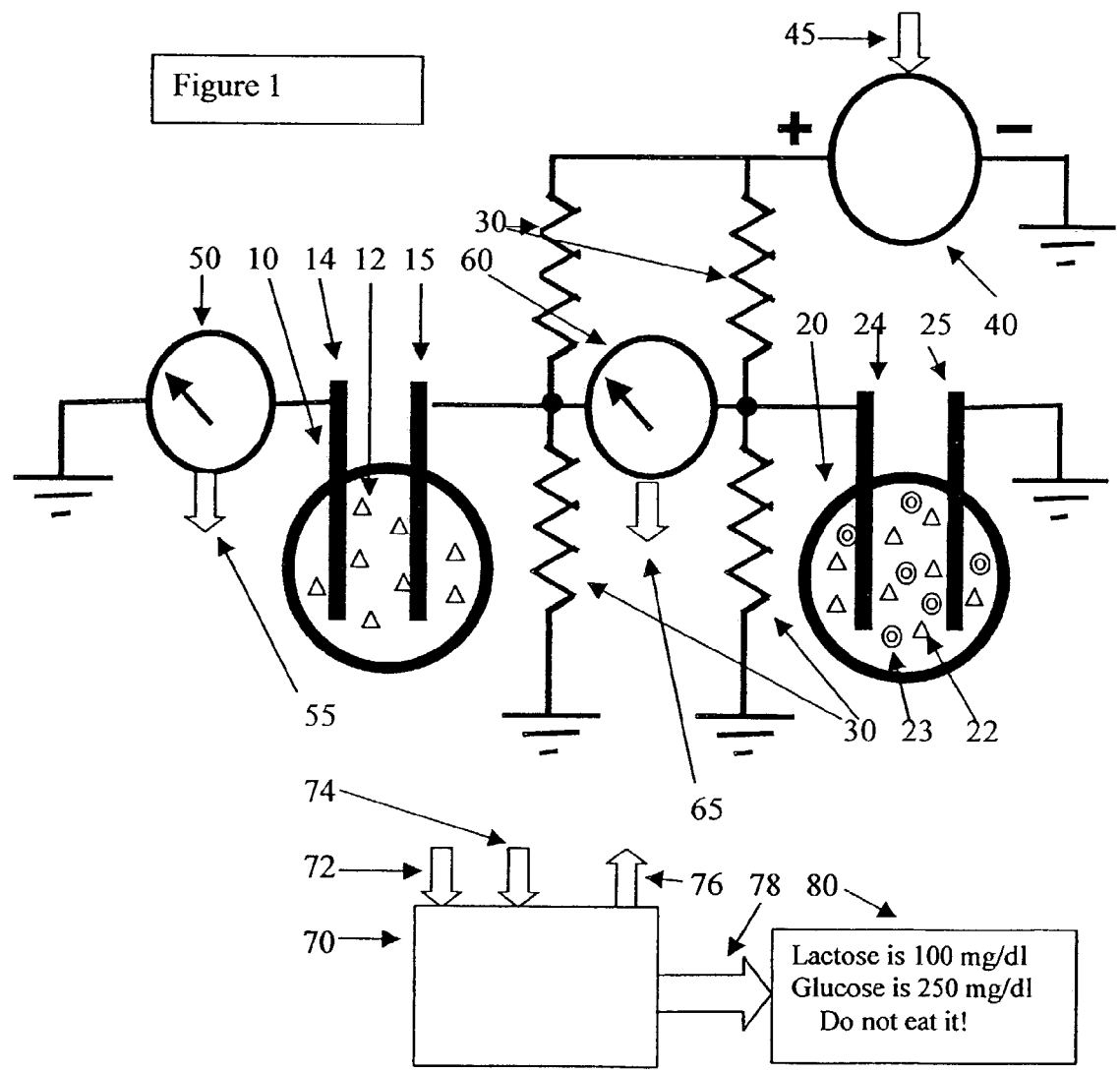

FIG. 1 shows a schematic drawing of a preferred embodiment of the present invention that is based on an electrolytic technique for detecting glucose. This preferred embodiment comprises a pair of test cells 10 and 20, a bridge balance circuit comprising four resistors 30, an electrical source 40, a glucose detection electrical meter 50, a lactose detection electrical meter 60, a computer 70 and a display devise 80. Each of the test cells 10 and 20 receive a sample of the food to be tested and sufficient water to fluidize the sample and dissolve the glucose and lactose that may be present. The test cell for measuring the background glucose content 10 is preloaded with glucose oxidase 12 which is also known as *Aspergillus niger*. This test cell 10 also comprises a pair of electrodes 14 and 15 which can be formed from platinum, graphite, or any other non reactive conductive material. This type of glucose test cell is the subject of much prior art including U.S. Pat. No. 4,545,382 and U.S. Pat. No. 4,711,245. According to the present invention, the lactose test cell 20 comprises a preload 22 of glucose oxidase and lactase enzyme 23, and a pair of electrodes 24 and 25 that also can be formed from platinum, graphite, or any other non-reactive electrically conductive material.

Operation of this preferred embodiment of the present lactose test invention proceeds by mixing the food sample with sufficient water to fluidize it and dissolve the glucose (and other monosacarides such as fructose) and lactose in it. The wet sample is then applied to the two test cells 10 and 20. The preload glucose oxidase enzyme 12 and 22 in the test cells 10 and 20 causes the glucose to oxidize in air to form gluconic acid and hydrogen peroxide. The electrical source 40 and the balanced bridge 30 are tuned to apply a potential of approximately 0.6V between the electrodes 14 and 15 and between the electrodes and 24 and 25 in test cells 10 and 20. This potential results in the electrolysis of any hydrogen peroxide that is present in the cells, due to the presence of glucose, into oxygen and hydrogen but is insufficient to electrolyze water significantly. The resulting currents in the two test cells 10 and 20 will be equal if there is an equal concentration of glucose in the two cells. The balance of the bridge circuit resistors 30 will result in no current in the imbalance detection lactose detector meter 60. However if there is lactose present the lactase enzyme preload 23 in the lactose detection cell 20 will convert it into glucose and galactose. Thus it will result in a greater concentration of glucose in test cell 20 due to the conversion of lactose into glucose and galactose. Therefore the lactose sensing cell 20 will pass more current than the glucose sensing cell 10. This extra current will imbalance the bridge 30 resulting in a current in the lactose detection imbalance meter 60 indicating the presence of lactose in the sample.

In this preferred embodiment a glucose sensing meter 50 is in series with the glucose sensing cell. Though meter 50 is not essential to the lactose detection process which results in a reading on the lactose detection meter 60, readings from meter 50 can be of value to the user by stating the quantity of glucose background there is in the food sample. A very high glucose background will result in greater measurement error in the lactose detection meter 60. Thus the glucose reading from the meter 50 can flag the existence of a larger margin of error on the reading from the lactose detection meter 60.

The computer 70 and the display devise 80 are optional feature of this preferred embodiment in that the user can directly evaluate the reading on the glucose detection meter 50 and the reading on the lactose detection meter 60 after a suitable stabilization pause of about 30 seconds. However the computer 70 can enhance user friendliness and accuracy by evaluating the time sequence of reading from the meters 50 and 60 transmitted on the data busses through meter output connections 55 and 65, which are connected to the computer inputs 72 and 74. The computer can also regulate the power source 40 through its output connection 76 to a control bus which is connected to the power source through connector 45. The computer can also evaluate the degree of inaccuracy that the glucose content of the sample induces in the lactose reading. It can also display instructions and messages to the user on the display devise 80 through its output bus 76.

Figure 2:
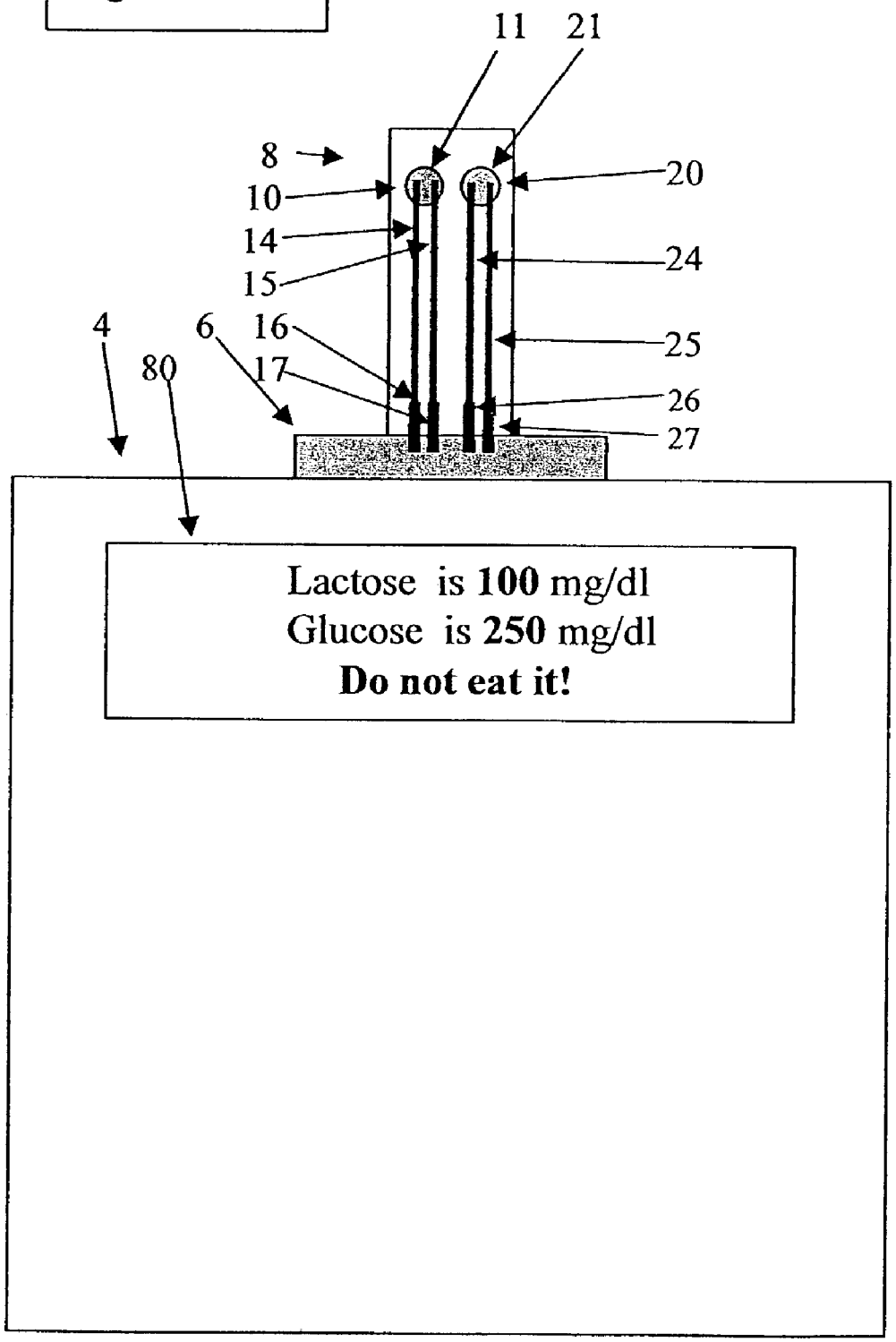

For the purpose of cost and convenience the test cells 10 and 20 should be formed on a disposable plastic strip 8 schematically illustrated in FIG. 2. The electrodes 14, 15, 24, and 25 are ideally formed by a printing process that uses a graphite based electrically conductive ink. The electrical contacts 16, 17, 26, and 27 to a matched connector 6 in the electronic unit 4 and the electrical leads on the plastic strip 8 are also formed of the same conductive ink. The electronic unit comprises the bridge circuit resistors 30, the power source 40, the meters 50 and 60, the computer 70 and the display screen 80 which are not shown in FIG. 2. The test cells 10 and 20 on the test strip 8 are preloaded during manufacture with the enzymes preloads 12, 22 and 23. The preloads are embedded in filter paper dots 11 and 21 that adhere to the plastic strip 8. They cover the electrodes 14 and 15 of cell 10 and 24, and 25 of cell 20.

With this arrangement the user simply inserts the test strip 8 into the connector 6 of the electronics unit 4 and then applies the wetted food sample to the test cells 10 and 20. The computer 70 then evaluates the time sequence of readings from the meters 50 and 60 and then displays the measured lactose and glucose contents on the display screen 80 along with advise on its consumption.

DETAILED DESCRIPTION OF A SECOND PREFERRED EMBODIMENTS OF THE INVENTION

Figure 3:
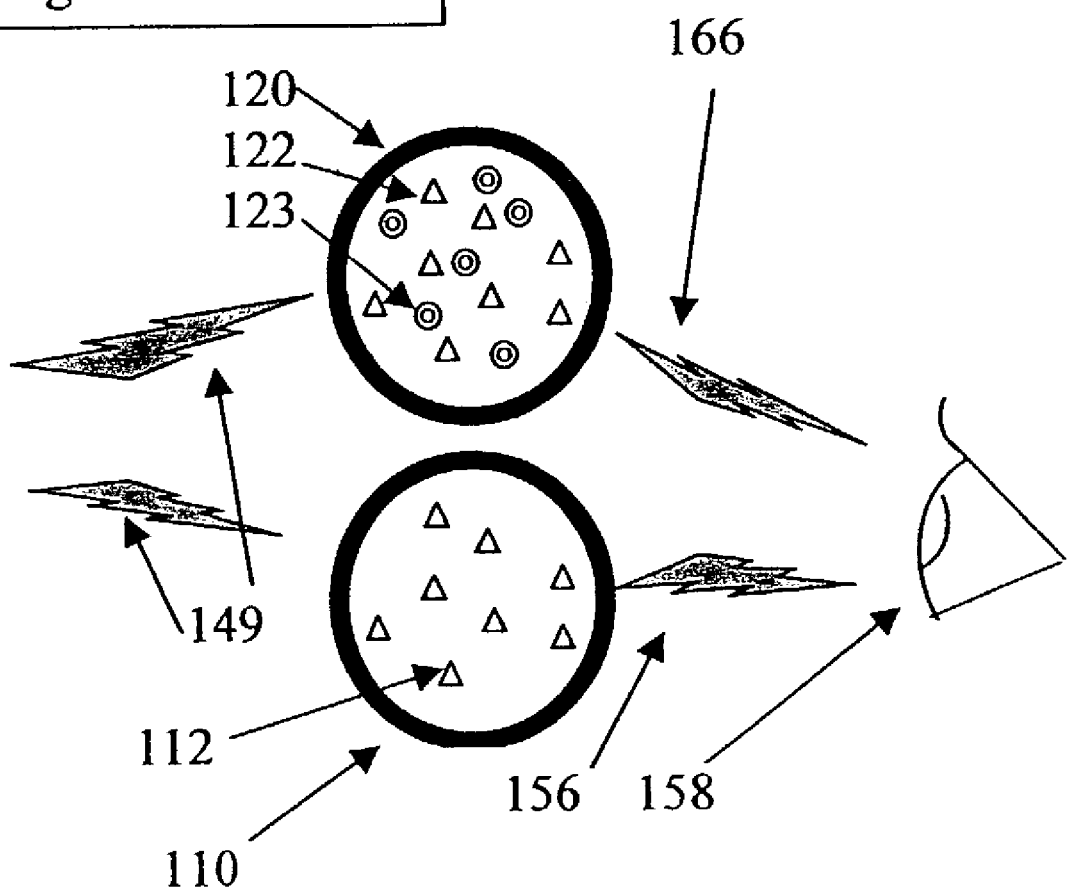
FIG. 3 shows a schematic drawing of a preferred embodiment of the present invention that is based on a visual technique for detecting glucose with the unaided eye 158.

We will now briefly describe the drawing for a second preferred embodiment of the present invention. FIG. 3 shows a schematic drawing of a preferred embodiment of the present invention that is based on a visual technique for detecting glucose with the unaided eye 158. This preferred embodiment comprises a pair of test cells 110 and 120. Each of the test cells 110 and 120 receive a sample of the food to be tested and sufficient water to fluidize the sample and dissolve the glucose and lactose that may be present.

The test cell for measuring the background glucose content 110 contains a preloaded glucose indicator 112 which comprises a glucose sensitive dye and additional chemicals that enhance the visual color change that results from the reactions between glucose and the preload 112. For example, the preload 112 might comprise the common antiseptic tincture of iodine. The presence of glucose will then result in a visible color change in test cell 110. If the ambient light 149 illuminating the test cells 110 and 120 is white, the reflected light 156 will be yellow-orange in the absence of glucose. The presence of glucose will alter this initial color to a brown-orange for a low glucose concentration. Higher concentrations will result in a brown color while very high concentrations will turn the test cell 110 black. A similar response will occur for the presence of fructose and other monosacarides.

The test cell 120 comprises the same glucose detection preload 122 as the preload 112 of the glucose test cell 110 and a preload 123 of lactase enzyme. Thus any lactose in the food subsample in the lactose test cell will be converted into an excess glucose concentration above that in the glucose detection cell 110. The glucose indicator preload will result in a deeper color in the reflected light 166 from the lactose detection cell 120 than that from the glucose detection cell 110. The deeper color change in the lactose detection cell 120 can be visually evaluated by the user with the unaided eye 157 if the glucose detection preloads 112 and 122 in test cells 110 and 120, respectively, comprise tincture of iodine or the mixture of ingredients described by Adams [1]. For example, a formulation similar to the teaching of Adams for a visual glucose test used by Clinistix test strips (manufactured by Bayer Corporation) comprises glucose oxidase. peroxidase, orthotoidine, and ph buffers.

DETAILED DESCRIPTION OF A THIRD PREFERRED EMBODIMENTS OF THE INVENTION

Figure 4:
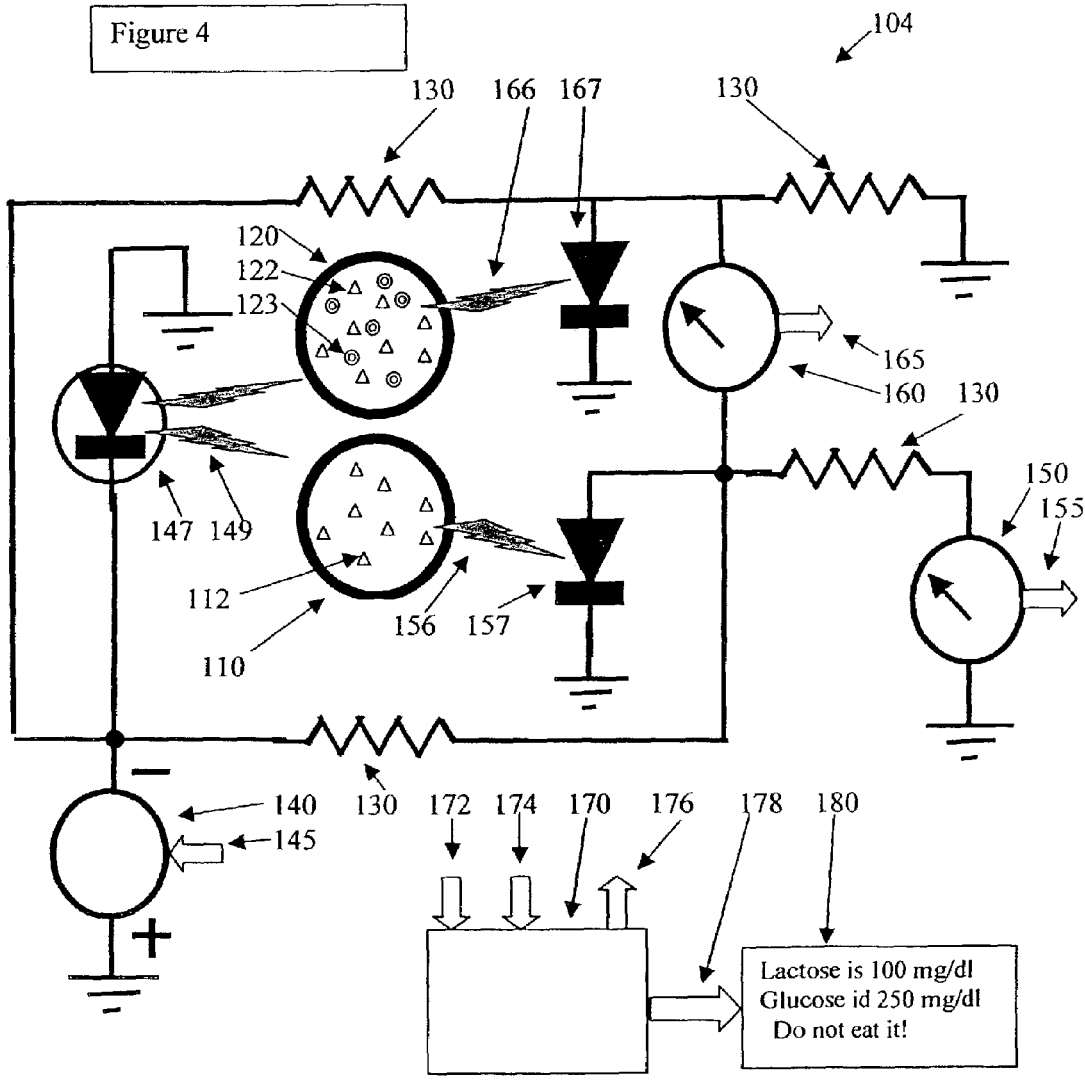
FIG. 4 shows an electronically based computer controlled color and intensity evaluation apparatus 104.

In order to improve the quantitative comparison between the depth of color changes in test cells 110 and 120 it is advantageous to provide an electronically based computer controlled color and intensity evaluation apparatus such as the lactose detection system 104 shown in FIG. 4. This preferred embodiment of the present invention comprises: a glucose test cell 110 with a glucose indicator preload 112; a lactose detecting test cell 120 with a glucose indicator 122 and lactase enzyme 123 preloads; a photo-luminescent diode 147; a glucose detector cell photo detector diode 157; a lactose detector cell photo detector diode 167; a bridge balance circuit comprised of four resistors 130; an electrical source 140; a glucose detection electrical meter 150; a lactose detection electrical meter 160; a computer 170; and a display devise 180.

In this apparatus 104 a power source 140 energizes the photo-luminescent diode 147. The light 149 emitted by the diode 147 shines uniformly on the test cells 110 and 120 after the wetted food subsamples have been applied. The reflected light 156 from test cell 110 then illuminates photo detector diode 157. Similarly, the reflected light 166 from test cell 120 illuminates photo detector diode 167. If there is no lactose in the sample there will be no excess glucose in test cell 120. Therefore, its reflectance will be the same as that of test cell 110 and the bridge circuit resistors 130 will result in no current in the lactose detection meter 160. If there is lactose present, the lactase preload 123 in test cell 120 will convert it into an excess of glucose concentration beyond that in test cell 110. The reduced reflectance of test cell 120 will result in reduced reflected light 166 and a reduced current in photo detector diode 167. This reduced current will imbalance the voltage across the resistors 130 the bridge circuit and thus result in a current in the lactose detection meter 160.

As in the electrolytic glucose detection preferred embodiment, an optional computer 70 can improve accuracy and user friendliness by evaluating the digitized meter reading transmitted from the meters through digital bus connections 155 and 165 to computer input ports 172 and 174. Computer output port 176 can control the power source 140 through its data control input port 145. The computer also displays instructions, test results, and advise on the display 80 through data bus 178.

Preload mixtures 112 and 122 are available which can provide good optical response in the infra red part of the optical spectrum. For infrared sensitive glucose indicator preloads, luminescent diode 147 would emit infra red and photodection diodes 157 and 167 would be sensitive to the same infra red part of the spectrum. An example of a suitable glucose indicator preload 112 and 122 used by the CVS Corporation for blood glucose detection comprises glucose oxidase, peroxidase, 4-aminoantipyrine, N-ethyl-N-(2-hydroxy-3-sulfopropyl)-3,5-dimethoxyanine, and buffers. This taught by U.S. Pat. No. 5,296,192, U.S. Pat. No. 5,509,410, U.S. Pat. No. 5,682,884, U.S. Pat. No. 5,820,551, and U.S. Pat. No. 5,727,548.

Figure 5:
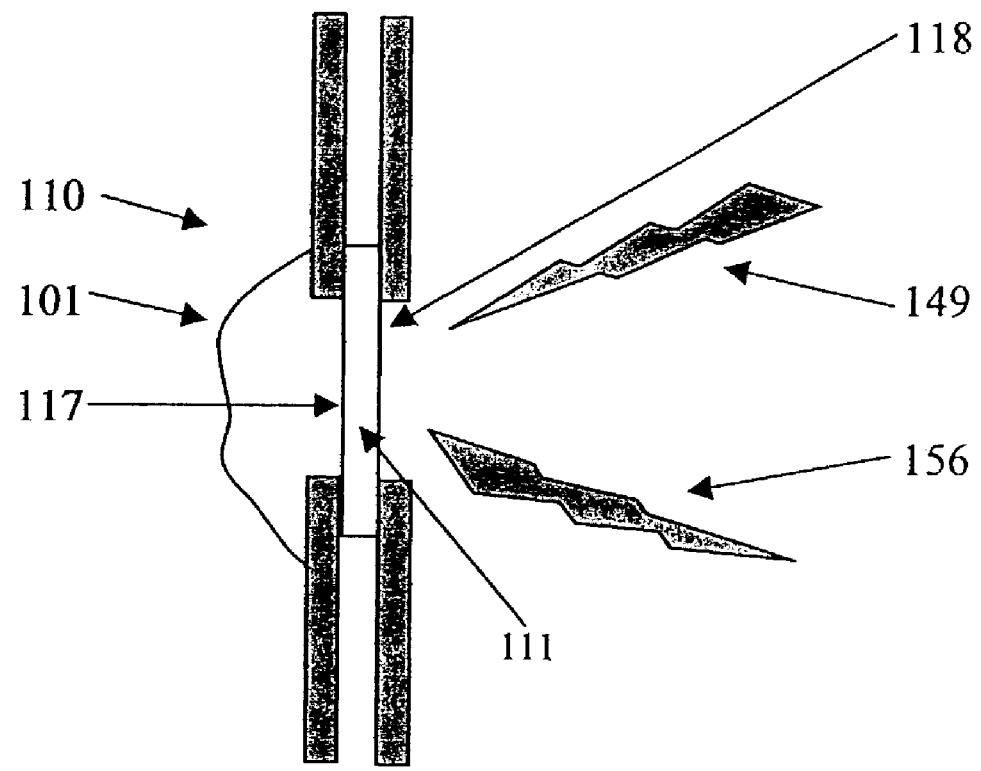
FIG. 5 shows optical detection of glucose.

Referring to FIG. 5, when optical detection of glucose is used by the present invention to detect lactose in food items it is important that the solid constituents of the food sample not interfere or block the glucose induced absorption of the incident light. Therefore, it is advantageous that the test cell 110 and 120 comprise small pieces of fine filter paper 111 and the preloads 112, 122, and 123. The user then applies the wetted food samples to a first side 117 of the filter paper while the observations of light absorption are carried out on the second side 118. The filter paper prevents the passage of opaque solids in the food sample that would interfere with the measurement.

While the invention has been described with reference to several embodiments it will be understood by those skilled in the art that modifications in details and form can be made without departing from the scope and spirit of the invention.

I claim:

1. A lactose test apparatus comprising:
   (a) a test cell containing a glucose indicator;
   (b) a means to add an agent that converts lactose to glucose to the said test cell; and
   (c) an apparatus to measure glucose concentration in said test cell before and after said addition of said lactose converting agent to said test cell.

2. The lactose test apparatus of claim 1, in which said glucose indicator alters the optical absorption properties of said test cell in the presence of glucose.

3. The lactose test apparatus of claim 2, in which said apparatus to measure glucose concentration of claim 1 further comprises:
   (a) a light source illuminating said test cell;
   (b) a means to measure the reflected light intensity from said test cell; and
   (c) a means to display the difference between the magnitudes of said reflected light intensity before and after adding an agent that converts lactose to glucose to said test cell.

4. The lactose test apparatus of claim 3, further comprising a means to display the initial magnitude of said reflected light intensity.

5. The lactose test apparatus of claim 1, in which said glucose indicator alters the electrolytic properties of said test cell in the presence of glucose and the said apparatus to measure glucose concentration further comprises:
   (a) a pair of electrodes in said test cell;
   (b) a means to apply an electrical potential between said electrodes;
   (c) a means to measure the electrolytic current of said test cell; and
   (d) a means to display the magnitude of said electrolytic current.

6. The lactose test apparatus of claim 5, further comprising a means to display the difference between the magnitudes of the electrolytic currents in said test cell of claim 1 between the initial value of said electrolytic current and the final value of said electrolytic current after the said addition of said agent that converts lactose to glucose in said test cell.

7. A lactose test apparatus comprising:
   (a) a test cell containing a glucose indicator in which said glucose indicator alters the optical absorption properties of said test cell in the presence of glucose; and
   (b) a test cell containing an agent that converts lactose to glucose and the same said glucose indicator.

8. A lactose test apparatus comprising:
   (a) a test cell containing a glucose indicator in which said glucose indicator alters the optical absorption properties of said test cell in the presence of glucose; and
   (b) a means to add an agent that converts lactose to glucose to the said test cell.

9. The lactose test apparatus of claim 8, in which said test cells further comprise a means to exclude solids from the optical detection surface of said test cell.

10. A lactose test apparatus of comprising:
(a) a first test cell containing a glucose indicator in which said glucose indicator alters the optical absorption properties of said test cell in the presence of glucose;
(b) a second test cell containing an agent that converts lactose to glucose and the same said glucose indicator; and
(c) an apparatus to measure glucose concentration in said test cells.

11. The lactose test apparatus of claim 10, in which said apparatus to measure glucose concentration further comprises:
(a) a light source illuminating said test cells;
(b) a means to measure the reflected light intensity from each of said test cells; and
(c) a means to display the magnitudes of said reflected light intensities.

12. The lactose test apparatus of claim 10, in which said apparatus to measure glucose concentration further comprises:
(a) a light source illuminating said test cells;
(b) a means to measure the reflected light intensity from each of said test cells; and
(c) a means to display the difference between the magnitudes of said reflected light intensities.

13. The lactose test apparatus of claim 12, further comprising a means to display the magnitude of the electrolytic current in said first test cell of claim 10.

14. The lactose test apparatus of claim 10, in which said test cells further comprise a means to exclude solids from the optical detection surface of said test cells.

15. A lactose test apparatus comprising:
(a) a first test cell containing a glucose indicator in which said glucose indicator alters the electrolytic properties of said test cell in the presence of glucose;
(b) a second test cell containing an agent that converts lactose to glucose and the same said glucose indicator;
(c) an apparatus to measure glucose concentration in said test cells and the said apparatus to measure glucose concentration further comprises:
(d) a pair of electrodes in each of said test cells;
(e) a means to apply an electrical potential between each of said electrode pairs;
(f) a means to measure the electrolytic current in each of said test cells; and
(g) a means to display the magnitude of said electrolytic currents.

16. A lactose test apparatus comprising:
(a) a first test cell containing a glucose indicator in which said glucose indicator alters the electrolytic properties of said test cell in the presence of glucose;
(b) a second test cell containing an agent that converts lactose to glucose and the same said glucose indicator;
(c) an apparatus to measure glucose concentration in said test cells and said apparatus to measure glucose concentration further comprises;
(d) a pair of electrodes in each of said test cells;
(e) a means to apply an electrical potential between each of said electrode pairs;
(f) a means to measure the electrolytic current in each of said test cells; and
(g) a means to display the difference in magnitude of said electrolytic currents.

17. The lactose test apparatus of claim 16, further comprising a means to display the magnitude of the electrolytic current in said first test cell.

18. A lactose test apparatus comprising:
(a) a test cell containing a glucose indicator which alters the optical absorption properties of said test cell in the presence of glucose;
(b) an agent that converts lactose to glucose; and
(c) a means to exclude solids from the optical detection surface of said test cell.

19. A lactose test apparatus comprising:
(a) a test cell containing a glucose indicator which alters the optical absorption properties of said test cell in the presence of glucose;
(b) an agent that converts lactose to glucose; and
(c) a means to exclude solids from the optical detection surface of said test cells.

20. A lactose test apparatus comprising:
(a) a test cell containing a glucose indicator which alters the optical absorption properties of said test cell in the presence of glucose;
(b) an agent that converts lactose to glucose; and
(c) a means to exclude solids from the optical detection surface of said test cell.

21. A lactose test apparatus comprising:
(a) a test cell containing a glucose indicator which alters the optical absorption properties of said test cell in the presence of glucose,
(b) a means to add an agent that converts lactose to glucose to the said test cell;
(c) an apparatus to measure glucose concentration in said test cell before and after said addition of said lactose converting agent to said test cell; and
(d) a means to exclude solids from the optical-detection surface of said test cell.

* * * * *